United States Patent [19]
Quincy et al.

[11] Patent Number: 5,455,108
[45] Date of Patent: Oct. 3, 1995

[54] COATED POLYMERIC FABRIC HAVING REDUCED ADSORPTION OF PROTEIN

[75] Inventors: Roger B. Quincy, III, Alpharetta; Ronald S. Nohr, Roswell; John G. MacDonald, Decatur; Dennis S. Everhart, Alpharetta, all of Ga.

[73] Assignee: Kimberly-Clark Corporation, Neenah, Wis.

[21] Appl. No.: 175,654

[22] Filed: Dec. 30, 1993

[51] Int. Cl.$^6$ .............................. B05D 3/06; B05D 5/08; B32B 33/00
[52] U.S. Cl. .............................. 428/266; 2/78.1; 2/400; 15/209.1; 427/538; 428/288; 428/289; 428/290; 428/447
[58] Field of Search .......................... 427/538; 428/266, 428/288, 289, 290, 447; 604/381

[56] References Cited

U.S. PATENT DOCUMENTS

| | | | |
|---|---|---|---|
| 4,535,020 | 8/1985 | Thomas | 428/131 |
| 5,112,690 | 5/1992 | Cohen et al. | 428/411.1 |
| 5,158,575 | 10/1992 | Czeh | 8/116.1 |

OTHER PUBLICATIONS

J. F. Carley, et al. "Corona–Discharge Treatment of Polymeric Films, II: Chemical Studies." *Polymer Engineering and Science*, Mar. 1980, vol. 20, No. 5, pp. 330–338.

J. J. Levitzky, et al. "Corona Discharge Treatment of Polypropylene Films." SPE Journal, Dec. 1964, pp. 1305–1308.

J. Adelsky "Effects of Corona Retreatment on Surface Characteristics of Oriented Polypropylene Films." *Tappi Journal*, Sep. 1989, pp. 181–184.

M. M. Kadash, et al. "Closer Characterization of Corona–Treated PE Surfaces." *Plastics Engineering*, Dec. 1985, pp. 45–48.

B. Catoire, et al. "A Study of Polyolefin Films and Yarns Under Corona Discharge." *Corona Electricity*, pp. 457–470.

G. P. Lopez, et al. "Glow Discharge Plasma Deposition of Tetraethylene Glycol Dimethyl Ether for Fouling–Resistant Biomaterial Surfaces." *J. of Biomedical Mat. Research*, V. 26, pp. 415–439, 1992.

J. H. Lee, et al., "Protein-Resistant Surfaces Prepared by PEO–Containing Block Copolymer Surfactants." *Journal of Biomedical Materials Research*, vol. 23, 1989, pp. 351–368.

R. W. Pekala, et al. "Fibrinogen Adsorption and Platelet Adhesion at the Surface of Modified Polypropylene Glycol/Polysiloxane Networks." *Biomaterials*, Sep. 1986, vol. 7, pp. 379–385.

E. L. Chaikof, et al., "Platelet Interaction with Poly(Ethylene Oxide)/Polysiloxane Networks." *Journal of Colloid and Interface and Interface Science*, vol. 137, No. 2, Jul. 1990, pp. 340–349.

A. Z. Piao, et al. "Synthesis and Characterization of PolyDimethylsiloxane)–Poly (Ethylene Oxide)–Heparin CBABC Type Block Copolymers." *J. of Biomaterial Science Polymer Edn.*, 1990, vol. 1, No. 4, pp. 299–313.

C. Sung, et al. "Synthesis and Characterization of Polymer Networks Made from Poly (Ethylene Oxice) and Polysiloxane." *Biomedical Net.–Macromolecular Chem.* 1990, V. 1, No. 4, pp. 266–268.

R. W. Pekala, et al. "Crosslinked Polyether/Polysiloxane Netwrks for Blood–Interfacing Applications." *Biomaterials*, Sep. 1986 vol. 7, pp.372–378.

E. L. Chaikof, et al. "Bulk Properties of Poly(Ethylene Oxide)/Polysiloxane Network." *Net Polymeric Material*, 1990. vol. 2, No. 2, pp. 125–147.

C. G. Golander, et al. "Properties of Immobilized PEG Films and the Interaction with Proteins Experiments and Modeling." *Poly (Ethylene Glycol) Chemistry: Biotechnical and Biomedical Applic.*, Plenum Press, N.Y. pp. 221–245.

E. W. Merrill "Poly(Ethylene Oxide) and Blood Contact–A Chronical of One Laboratory." *Poly(Ethylene Glycol) Chemistry: Biotechnical and Biomedical Applications*, Plenum Press, N. Y. 1992, pp. 199–220.

D. Kiaei, et al. "Immobilization of Proteins on Glow Dishcarge Treated Polymers." *Radiat. Phys. Chem.*, V. 39, No. 6, pp. 463–467, 1992.

D. Kiaei, et al. "Ex Vivo and in Vitro Platelet Adhesion on RFGD Deposited Polymers." *Journal of Biomedical Materials Research*, vol. 26, pp. 357–372, 1992.

M. S. Sheu, et al. "A Glow Discharge Treatment to Immobilize Poly(Ethylene Oxide)/Poly(Propylene Oxide) Surfactants for Wettable and Non–Fouling Biomaterial." *J. Adhesion Sci. Technol.*, vol. 6, No. 9, pp. 995–1009, 1992.

M. S. Sheu, et al. "A New Gas Discharge Process for Preparation of Non–Fouling Surfaces on Biomaterials," *Clinical Materials*, pp. 41–45, 1993.

Chaikof, E. L., "Polyethylene Oxide/Polysiloxane Interpenetrating Polymer Networks for Blood Contact." *Massachusetts Institute of Technology*, (Submitted in partial fulfillment of the requirements for the Degree of Doctor of Philosophy), 1989, pp. 1–3. [Abstract].

Sung, C., "A Study of Polyethylene Oxide–Polysiloxane Networks as Biomaterials for Drug Release." *Massachusetts Institute of Technology*, 1988 (Submitted in partial fulfillment of the requirements for the Degree of Doctor of Philosophy), pp. 1–2. [Abstract].

*Primary Examiner*—James C. Cannon
*Attorney, Agent, or Firm*—William E. Maycock

[57] ABSTRACT

A method of reducing the adsorption of protein by a polymeric fabric; e.g., a polyolefin fabric, which involves providing a polymeric fabric having a surface, applying to the surface of the polymeric fabric a composition including water and a surfactant adapted to reduce the adsorption of protein by the polymeric fabric, and treating the fabric to which a surfactant has been applied by air corona discharge at a corona energy density of from about 10 to about 280 kilojoules per square meter. The surfactant is present on the fabric in an amount sufficient to reduce the adsorption of protein by the fabric. The coated fabric is especially suited for incorporation in such disposable absorbent articles as diapers; feminine care products, such as sanitary napkins and tampons; incontinent care products; training pants; and wipes.

20 Claims, 3 Drawing Sheets

COATED POLYMERIC FABRIC HAVING REDUCED ADSORPTION OF PROTEIN

BACKGROUND OF THE INVENTION

The present invention relates to a coated polymeric fabric.

Polymers are used extensively to make a variety of products which include blown and cast films, extruded sheets, injection molded articles, foams, blow molded articles, extruded pipe, monofilaments, and nonwoven webs. Some of such polymers, such as polyolefins, are naturally hydrophobic, and for many uses this property is either a positive attribute or at least not a disadvantage.

There are a number of uses for polymers, however, where their hydrophobic nature either limits their usefulness or requires some effort to modify the surface characteristics of the shaped articles made therefrom. By way of example, polyolefins, such as polyethylene and polypropylene, are used to manufacture polymeric fabrics which are employed in the construction of such disposable absorbent articles as diapers, feminine care products, incontinence products, training pants, wipes, and the like. Such polymeric fabrics often are nonwoven webs prepared by, for example, such processes as meltblowing, coforming, and spunbonding; they have a pronounced tendency to adsorb protein. When these fabrics are employed in the construction of such disposable absorbent articles as diapers, feminine care products, incontinence products, training pants, wipes, and the like, the tendency to adsorb protein often is deemed to be a disadvantage. This is particularly true in the case of feminine care and other products which come in contact with blood and other colored-protein-containing fluids. The adsorption of colored proteins by a component of the product contributes to disapproval of the product for aesthetic reasons, even though the product may have superior performance in its intended function of fluid absorption and redistribution. More importantly, however, the adsorption of protein often reduces or prevents fluid absorption.

In the past, resistance to the adsorption of protein by a polymeric (or other) material has been accomplished by, for example, the radio frequency glow discharge plasma deposition of tetraethylene glycol dimethyl ether onto a polymeric material; coating of a polymeric material with polyethylene oxide-containing block copolymer surfactants or a polyethoxylated alkylphenol or long-chain aliphatic alcohol, with or without an argon radio frequency glow discharge treatment after the polymeric material has been coated; immobilization of baboon albumin on radio frequency glow discharge-treated surfaces; radio frequency glow discharge polymerization of monomers on the surface of a material; a coating of a crosslinked polypropylene glycol/polyglycidoxy propyl methyl siloxane network which contains polyethylene glycol monomethyl ether chains; use of interpenetrating polymer networks of poly(ethylene oxide) and a polyether substituted polysiloxane; use of poly(dimethylsiloxane)-poly(ethylene oxide)-heparin CBABC type block copolymers; and use of immobilized poly(ethylene glycol) films.

Notwithstanding the advances which have been made in providing surfaces which are resistant to the adsorption of protein by a polymeric material, there still is a need for further improvement.

SUMMARY OF THE INVENTION

It therefore is an object of the present invention to provide a method of reducing the adsorption of protein by a polymeric fabric.

It is another object of the present invention to provide a coated polymeric fabric.

It is a further object of the present invention to provide a disposable absorbent article, at least one component of which is the coated polymeric fabric of the present invention.

These and other objects will be apparent to those having ordinary skill in the art from a consideration of the specification and claims which follow.

Accordingly, the present invention provides a method of reducing the adsorption of protein by a polymeric fabric which includes:

providing a polymeric fabric having a surface;

applying to the surface of the polymeric fabric a composition comprising water and a surfactant adapted to reduce the adsorption of protein by the polymeric fabric; and treating the fabric to which the composition has been applied by air corona discharge at a corona energy density of from about 10 to about 280 kilojoules per square meter.

The present invention also provides a coated polymeric fabric which includes:

a base ply of a polymeric fabric having a surface; and a surfactant on the surface of the fabric; in which the surfactant is adapted to reduce the adsorption of protein by the polymeric fabric and is present on the fabric in an amount of at least about 0.3 percent by weight, based on the weight of the fabric, and the coated polymeric fabric has been treated by air corona discharge at a corona energy density of from about 10 to about 280 kilojoules per square meter.

The present invention additionally provides a coated polymeric fabric which includes:

a base ply of a polymeric fabric having a surface; and a surfactant on the surface of the fabric; in which the surfactant is present on the fabric in an amount of at least about 0.3 percent by weight, based on the weight of the fabric and has the general formula, $$R_1-\underset{\underset{R_3}{|}}{\overset{\overset{R_2}{|}}{Si}}-O-(\underset{\underset{R_5}{|}}{\overset{\overset{R_4}{|}}{Si}}-O)_a-(\underset{\underset{CH_2}{|}}{\overset{\overset{R_6}{|}}{Si}}-O)_b-\underset{\underset{R_9}{|}}{\overset{\overset{R_7}{|}}{Si}}-R_8$$
$$|\\(CH_2)_cO(C_3H_6O)_d(C_2H_4O)_eR_{10}$$

wherein:

each of $R_1$–$R_9$ independently is selected from the group consisting of $C_1$–$C_8$ alkyl and aryl groups;

$R_m$ is hydrogen or a $C_1$–$C_4$ alkyl group;

a represents an integer from about 20 to about 100;

b represents an integer from about 4 to about 20;

c represents an integer from 1 to about 10;

d represents an integer from about 0 to about 30;

e represents an integer from about 0 to about 30;

the sum of d and e is in a range of from about 5 to about 60; and the number-average molecular weight of the surfactant is in a range of from about 5,000 to about 60,000; and the coated polymeric fabric has been treated by air corona discharge at a corona energy density of from about 10 to about 280 kilojoules per square meter.

The present invention further provides a disposable absorbent article, at least one component of which is the coated polymeric fabric of the present invention. Examples of disposable absorbent articles include diapers; feminine care products, such as sanitary napkins and tampons; incontinent care products; training pants; and wipes.

DETAILED DESCRIPTION OF THE INVENTION

Figure 1:
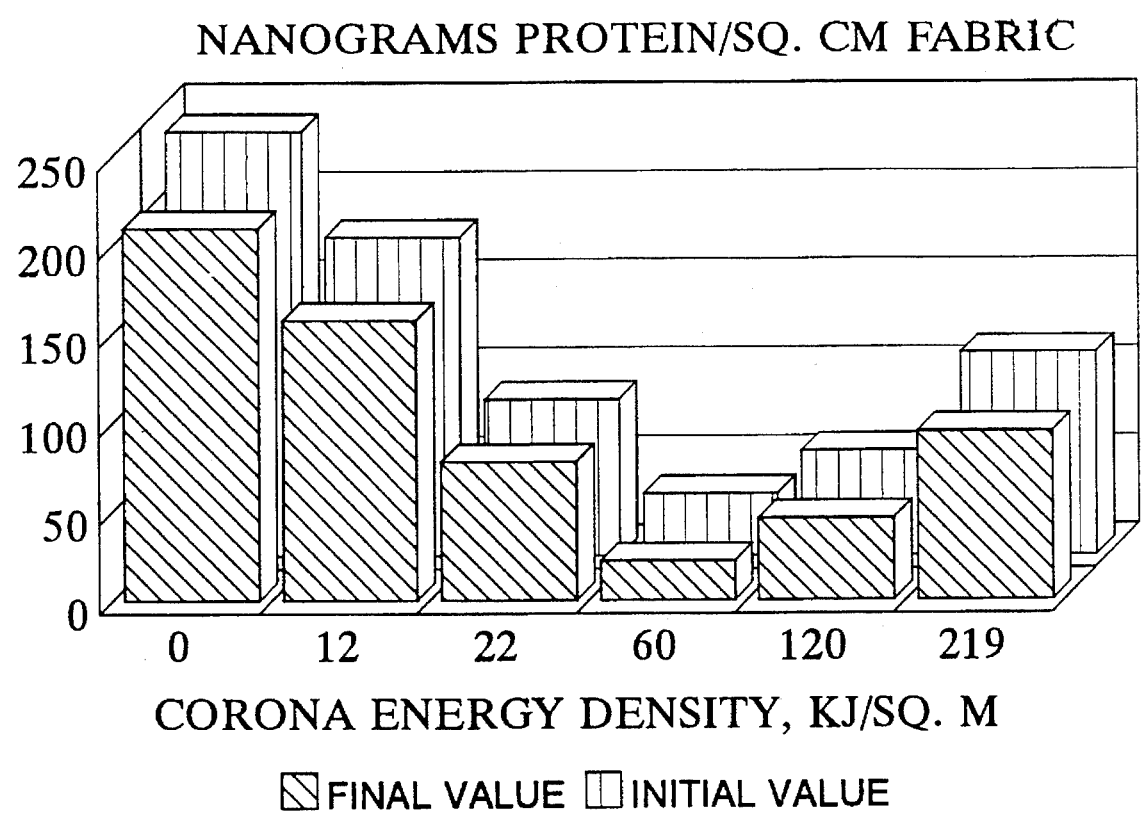
FIGS. 1 and 2 are three-dimensional bar graphs showing initial and final amounts of protein adsorbed on polymeric fabrics to which two different surfactants have been applied, as measured by a radiolabeling technique, as a function of corona energy density.

The term "protein" is meant to include any protein, including both simple proteins and such conjugated proteins as, by way of example only, nucleoproteins, lipoproteins, glycoproteins, phosphoproteins, hemoproteins, flavoproteins, and metalloproteins. Thus, the term is meant to encompass, without limitation, enzymes, storage proteins, transport proteins, contractile proteins, protective proteins, toxins, hormones, and structural proteins, by way of illustration only.

As used herein, the term "polymeric fabric" means a fabric prepared from any polymeric material capable of being formed into a fabric. Thus, such material can be synthetic or natural, although the former are more likely to be employed in the present invention. Examples of natural polymeric materials include, cotton, silk, wool, and cellulose, by way of illustration only.

Synthetic polymeric materials, in turn, can be either thermosetting or thermoplastic materials, with thermoplastic materials being more common. Examples of thermosetting polymers include, by way of illustration only, alkyd resins, such as phthalic anhydride-glycerol resins, maleic acid-glycerol resins, adipic acid-glycerol resins, and phthalic anhydride-pentaerythritol resins; allylic resins, in which such monomers as diallyl phthalate, diallyl isophthalate diallyl maleate, and diallyl chlorendate serve as nonvolatile cross-linking agents in polyester compounds; amino resins, such as aniline-formaldehyde resins, ethylene urea-formaldehyde resins, dicyandiamide-formaldehyde resins, melamineformaldehyde resins, sulfonamide-formaldehyde resins, and urea-formaldehyde resins; epoxy resins, such as cross-linked epichlorohydrin-bisphenol A resins; phenolic resins, such as phenol-formaldehyde resins, including Novolacs and resols; and thermosetting polyesters, silicones, and urethanes.

Examples of thermoplastic polymers include, by way of illustration only, end-capped polyacetals, such as poly(oxymethylene) or polyformaldehyde, poly(trichloroacetaldehyde), poly(n-valeraldehyde), poly(acetaldehyde), poly(propionaldehyde), and the like; acrylic polymers, such as polyacrylamide, poly(acrylic acid), poly(methacrylic acid), poly(ethyl acrylate), poly(methyl methacrylate), and the like; fluorocarbon polymers, such as poly(tetrafluoroethylene), perfluorinated ethylene-propylene copolymers, ethylene-tetrafluoroethylene copolymers, poly(chlorotrifluoroethylene), ethylene-chlorotrifluoroethylene copolymers, poly(vinylidene fluoride), poly(vinyl fluoride), and the like; polyamides, such as poly(6-aminocaproic acid) or poly(ε-caprolactam), poly(hexamethylene adipamide), poly(hexamethylene sebacamide), poly(11-aminoundecanoic acid), and the like; polyaramides, such as poly(imino-1,3-phenyleneiminoisophthaloyl) or poly(m-phenylene isophthalamide), and the like; parylenes, such as poly-p-xylylene, poly(chloro-p-xylylene), and the like; polyaryl ethers, such as poly(oxy-2,6-dimethyl-1,4-phenylene) or poly(p-phenylene oxide), and the like; polyaryl sulfones, such as poly(oxy-1,4-phenylenesulfonyl-1,4-phenyleneoxy-1,4-phenylene-isopropylidene-1,4-phenylene), poly(sulfonyl-1,4-phenyleneoxy-1,4-phenylenesulfonyl-4,4'-biphenylene), and the like; polycarbonates, such as poly(bisphenolA)or-poly(carbonyldioxy-1,4-phenyleneisopropylidene-1,4-phenylene), and the like; polyesters, such as poly(ethylene terephthalate), poly-(tetramethylene terephthalate), poly(cyclohexylene-1,4-dimethylene terephthalate or poly(oxymethylene-1,4-cyclohexylenemethyleneoxyterephthaloyl), and the like; polyaryl sulfides, such as poly(p-phenylene sulfide) or poly(thio-1,4-phenylene), and the like; polyimides, such as poly(pyromellitimido-1,4-phenylene), and the like; polyolefins, such as polyethylene, polypropylene, poly(1-butene), poly(2-butene), poly(1-pentene), poly(2-pentene), poly(3-methyl-1-pentene), poly(4-methyl-l-pentene), 1,2-poly-1,3-butadiene, 1,4-poly-1,3-butadiene, polyisoprene, polychloroprene, polyacrylonitrile, poly(vinyl acetate), poly(vinylidene chloride), polystyrene, and the like; copolymers of the foregoing, such as acrylonitrile-butadiene-styrene (ABS) copolymers, and the like; and the like. In certain embodiments, the polymeric fabric will be prepared from a polyolefin. In other embodiments, the polyolefin will be polypropylene.

The term "fabric" is used broadly herein to mean any fibrous material which has been formed into a sheet or web. That is, the fabric is composed, at least in part, of fibers of any length. Thus, the fabric can be a woven or nonwoven sheet or web, all of which are readily prepared by methods well known to those having ordinary skill in the art. For example, nonwoven webs are prepared by such processes as meltblowing, coforming, spunbonding, carding, air laying, and wet laying. Moreover, the fabric can consist of a single layer or multiple layers. In addition, a multilayered fabric can include films, scrim, and other nonfibrous materials.

The term "surfactant" is used herein to mean any surface-active agent which is capable of imparting to a polymeric fabric protein antifouling characteristics, i.e., a reduced tendency to adsorb protein. In certain embodiments, the surfactant has a solubility in water at 20° C. no greater than about 10 percent by weight, based on the weight of the water. In other embodiments, the surfactant has a solubility in water at 20° C. no greater than about 5 percent by weight, based on the weight of the water. In still other embodiments, the surfactant is a polysiloxane polyether having the general formula,

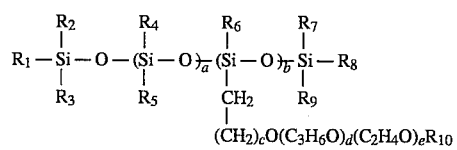

wherein:
  each of $R_{10}$–$R_9$ independently is selected from the group consisting of $C_1$–$C_8$ alkyl and aryl groups;
  $R_{10}$ is hydrogen or a $C_1$–$C_4$ alkyl group;
  a represents an integer from about 20 to about 100;

b represents an integer from about 4 to about 20;

c represents an integer from 1 to about 1 0;

d represents an integer from about 0 to about 30;

e represents an integer from about 0 to about 30;

the sum of d and e is in a range of from about 5 to about 60; and the number-average molecular weight of the surfactant is in a range of from about 5,000 to about 60,000.

In still other embodiments, each of $R_1$–$R_9$ independently is selected from the group consisting of $C_1$–$C_4$ alkyl and phenyl groups;

$R_{10}$ is hydrogen or a $C_1$–$C_4$ alkyl group;

a represents an integer from about 30 to about 90;

b represents an integer from about 4 to about 10;

c represents an integer from 2 to about 4;

d represents an integer from about 5 to about 25;

e represents an integer from about 5 to about 25;

the sum of d and e is in a range of from about 10 to about 50;

the ratio of e to d is in a range of from about 10 to about 0.1; and the number-average molecular weight of the surfactant is in a range of from about 5,000 to about 40,000.

In yet other embodiments, each of $R_1$–$R_9$ is a methyl group;

$R_{10}$ is hydrogen;

a represents an integer from about 40 to about 85;

b represents an integer from about 4 to about 8;

c represents an integer from 2 to about 4;

d represents an integer from about 15 to about 25;

e represents an integer from about 15 to about 25;

the sum of d and e is in a range of from about 30 to about 50;

the ratio of e to d is in a range of from about 5 to about 0.5; and the number-average molecular weight of the surfactant is in a range of from about 5,000 to about 30,000.

While the composition which is applied to the polymeric fabric is described in terms of water and a surfactant, it should be apparent to those having ordinary skill in the art that the term "surfactant" is meant to include both a single surfactant and a mixture of two or more surfactants as defined above. Thus, the term "composition" is used herein to mean a mixture (e.g., a solution or a dispersion) of one or more surfactants in water. The composition sometimes is referred to herein as the "surfactant composition."

As used herein, the term "energy density" refers to the energy absorbed as a function of electrode width and the rate at which the fabric passes through the corona. Energy density is calculated by dividing the output power in kilowatts by the width of the electrodes in meters and then by the line speed in meters per second, followed by multiplying the resulting value by the number of times the fabric is passed between the electrodes. The result is energy density in kilowatt-second per square meter, which is equivalent to kilojoules per square meter, kJ $m^{-2}$.

The method of the present invention is directed to reducing the adsorption of protein by a polymeric fabric. Such method involves:

providing a polymeric fabric having a surface;

applying to the surface of the polymeric fabric a composition which includes water and a surfactant adapted to reduce the adsorption of protein by the polymeric fabric, wherein the surfactant has a solubility in water at 20° C. no greater than about 5 percent by weight, based on the weight of the water; and treating the fabric to which the composition has been applied by air corona discharge at a corona energy density of from about 10 to about 280 kJ $m^{-2}$.

In the first step of the present invention, a polymeric fabric as already defined is provided. To the fabric then is applied a composition which includes water and a surfactant as already defined. The level of the surfactant in the composition can vary over a wide range. In general, the level of the surfactant is a function of the amount of the surfactant which is desired to be added to the polymeric fabric. As a practical matter, the level of the surfactant in the composition typically will be in a range of from about 0.1 to about 3 percent by weight, based on the weight of water. Depending on the level of add-on desired, however, lower or higher levels can be employed. As used herein, the term "add-on" refers to the weight percent of surfactant on a dry weight basis which coats the fibers of the polymeric fabric.

The composition which includes water and a surfactant can be applied to a surface of the polymeric fabric by any means known to those having ordinary skill in the art. Such means include, by way of illustration only, dipping, doctor blading, spraying, and direct and offset gravure printing or coating.

The amount of surfactant present on the polymeric fabric in general will be at least about 0.3 percent by weight, based on the weight of the polymeric fabric. As a practical matter, the amount of surfactant present typically will be in a range of from about 0.5 to about 10 percent by weight. In certain embodiments, the amount of surfactant present on the fabric will be in a range of from about 0.5 to about 7 percent by weight. In other embodiments, the amount of surfactant present on the fabric will be in a range of from about 0.5 to about 3 percent by weight.

After the surfactant composition has been applied to the polymeric fabric, the resulting coated fabric is treated by air corona discharge at a corona energy density of from about 10 to about 280 kJ $m^{-2}$. In general, any of the commercially available laboratory or production corona discharge units can be employed. Depending upon the power rating of the unit and the rate at which the unit passes a material under the corona source, a single pass may be appropriate. However, additional passes may be necessary to achieve the desired energy density with any given unit. In some embodiments, the corona energy density will be in a range of from about 35 to about 140 kJ $m^{-2}$.

The corona discharge treatment is carried out in air. While super- or sub-atmospheric pressure may be used if desired, the corona discharge treatment typically will be carried out at ambient, i.e., atmospheric, pressure. Moreover, the treatment typically will be carried out at ambient temperature, although the treating environment may be heated above or cooled below ambient temperature, if desired. While the effect of the temperature of the treating environment was not studied, it is possible that increasing the temperature of the treating environment may permit reductions in the corona energy density.

If desired, the polymeric fabric may be dried either before or after the corona treatment. Drying of the treated polymeric fabric can be accomplished by any known means. Examples of known drying means include, by way of illustration only, convection ovens, radiant heat, infrared radiation, forced air ovens, and heated rolls or cans. Drying also includes air drying without the addition of heat energy, other than that present in the ambient environment. In addition, the polymeric fabric also may be washed either before or after the corona treatment.

The coated polymeric fabric which is obtained after being treated by corona discharge exhibits a reduced tendency to adsorb protein, compared with either the identical fabric which has not been coated with the surfactant and subjected to corona discharge or the identical fabric which has been coated with the surfactant but has not been subjected to corona discharge.

The coated polymeric fabric of the present invention is suitable as a component of a disposable absorbent article. Examples of disposable absorbent articles include, by way of illustration only, diapers; feminine care products, such as sanitary napkins and tampons; incontinent products; training pants; and wipes.

The present invention is further described by the example which follows. Such example, however, is not to be construed as limiting in any way either the spirit or the scope of the present invention. In the example, all parts are by weight, unless stated otherwise.

EXAMPLE

The polymeric fabrics employed in this example were a spunbonded polypropylene nonwoven web having a basis weight of 1.0 ounce per square yard, or osy (about 24 grams per square meter, or g/m$^2$), Fabric A, and a spunbonded polypropylene nonwoven web having a basis weight of 1.6 osy (about 38 g/m$^2$), Fabric B.

Two surfactants were employed. The first, Surfactant A, was a polysiloxane polyether having the formula,

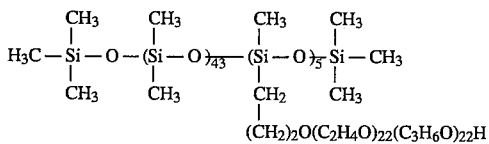

The material had a number-average molecular weight of 7,700, a weight-average molecular weight of 17,700, a z-average molecular weight of 27,700, and a polydispersity of 2.3. The surfactant composition was prepared by mixing 20.0 g of the surfactant with 2,000 g of distilled water and stirring at ambient temperature for about 60 minutes.

The second surfactant, Surfactant B, was similar to Surfactant A. The material had a number-average molecular weight of 13,000. The polyether side chains consisted of 77 percent by weight ethylene oxide and 23 percent by weight propylene oxide and the sum of ethylene oxide and propylene oxide repeating units was greater than 20. The material also contained about 80 dimethylsilyleneoxy repeating units. The surfactant composition was prepared by mixing 20.2 g of the surfactant with 2,100 g of distilled water and stirring at ambient temperature for about 3 hours.

Pieces of fabric measuring 8 inches by 8 inches (about 18 cm by 18 cm) were weighed and soaked in about 1,000 ml of the surfactant composition for about 5 minutes at ambient temperature. Two or three pieces of the fabric were soaked together in each 1,000-ml portion of surfactant composition. Each piece of fabric was removed from the composition and passed without folding through an Atlas Laboratory Wringer having a 40-lb (18.2-kg) nip setting. The piece of fabric then was allowed to air dry in a fume hood overnight and was weighed again.

The add-on of surfactant was calculated as a percentage based on the original dry weight of the sample as follows:

Percent add-on=100×(g TPF−g PF)/g PF wherein "g TPF" refers to the dry weight of the polymeric fabric to which the surfactant composition has been applied and "g PF" refers to the dry weight of the original fabric sample. The percent add-on was 2.6±0.2 for Surfactant A and 2.7 for Surfactant B.

Corona treatments were carried out with Corotec Laboratory Corona Treating Station with a CXC-5 Power Supply (Corotec Corporation, Collinsville, Conn.). The Treating Station utilized a pair of rotating metal rolls as electrodes, with the axes of the rolls lying in a vertical plane. Both rolls had a circumference of 12 inches (about 30.5 cm) and a diameter of about 3.8 inches (about 9.7 cm). The top roll was the anode and the bottom roll was the cathode. The bottom roll was fitted with a 2-mm-thick rubber dielectric sleeve which was in contact with the top roll, thereby providing a space of 2 mm between the electrodes. The top roll was 13 inches (about 33 cm) long and the bottom roll was about 16 inches (about 40.6 cm) long. The rolls rotated in opposite directions at a linear velocity of 12 feet per minute (about 6.1 cm per second).

Treated fabric, i.e., fabric to which surfactant has been applied, was subjected to corona discharge at varying energy densities. In addition, virgin Fabric B, that is, Fabric B to which a surfactant had not been applied, also was treated by corona discharge at an intermediate energy density as a positive control. Negative controls consisted of virgin fabric and fabric to which surfactant had been applied but which had not been corona treated.

Each piece of fabric to be tested for protein adsorption, including fabric which had been treated by corona discharge, was cut into approximately 11-mm× 50-mm strips and placed in 10-ml test tubes, one strip per tube. Distilled water at ambient temperature was added to each tube to a level about 3 mm below the top of the tube. The strip of treated fabric was completely immersed below the level of the water. After no less than 30 minutes (typically after about 40 minutes), the water was removed from each tube by aspiration and replaced with fresh distilled water. After about two hours, the water again was removed from the test tube. The fabric strip in each tube then was rinsed three times by successively filling the tube with distilled water and removing the water by aspiration. The fabric strips were left in the test tubes in a fume hood and allowed to air dry. In order to determine the amount of surfactant remaining on each fabric after the washing procedure, larger samples were subjected to the washing procedure, allowed to dry, and weighed.

The resulting samples were used for the fibrinogen protein adsorption experiments described below. The experiments were carried out in the laboratories of Prof. Allan S. Hoffman, Sc. D., Center for Bioengineering, University of Washington.

Fibrinogen from the baboon, *Papio cynocephalus*, was purified from citrated plasma supplied by the Regional Primate Research Center, University of Washington. Purification followed the poly(ethylene glycol)-β-alanine, fractional-precipitation method developed for bovine fibrinogen by Weathersby et al. (*Thromb. Res.* 10:245–252, 1977), with the exception that aprotinin, an inhibitor of serine proteases (Pohl, Methods Enzymol. 182:68–83, 1990; Trasylol®, Mobay Chemical Company, New York, N.Y.), was added to the plasma at 40 Kunitz inhibitory units/ml (e.g., Horbert et al., *J. Biomed. Mater. Res.* 20:739–772, 1986; Bohnert et al., *J. Biomater. Sci. Polym. Ed.* 1:279–297, 1990; and Sheu, Unpublished Ph.D. dissertation, University of Washington, Seattle, 1992).

Except where noted otherwise, purified fibrinogen was dissolved in a pH 7.4 buffer comprising 0.01M sodium citrate to prevent clotting due to contaminating proteases, 0.01M dibasic sodium phosphate, 0.12M sodium chloride, and 0.02 percent sodium azide as a bacteriostatic agent (Bohnert et at. 1990). This buffer will be referred to herein as cPBSz. During dialysis, presoaking, adsorption, displacement rinsing, and the final 24-hour soak-rinse, 0.01M sodium iodide was added to block sites for potential non-specific binding of iodide (Sheu 1992:66). This buffer is referred to herein as cPBSzI. To maintain a constant ionic strength, sodium chloride was reduced to 0.11 M in cPBSzI.

The concentration of pooled fibrinogen was evaluated by spectrophotometry. Samples were diluted to approximately 0.3 to 0.5 mg/ml, and the concentration determined based on absorbance at 280 nm (Mihalyi, *Biochem.* 7:208–222, 1968).

Fibrinogen samples were iodinated by the iodine monochloride method, as modified by Horbett (*J. Biomed. Mater. Res.* 15:673–695, 1981) and Bergström et al. (*J. Biomed. Mater. Res.* 26:779–790, 1992). This method employed equimolar fibrinogen and iodine monochloride. As the reaction proceeded, $^{125}I$ was linked to the tyrosine residues in fibrinogen ortho to the phenolic hydroxy group.

The reaction mixture was then purified by size-exclusion chromatography on Biogel P4®(poly(acryamide-co-N,N'-methylene bisacrylamide); Bio-Rad laboratories, Richmond, California). This gel filtration gave a good separation of bound and unbound iodine. The peak fractions (1.775 ml/fraction) of radiolabeled fibrinogen were pooled, then dialyzed extensively against cPBSzI using a cellulose-ester membrane (molecular-weight cutoff 12,000–14,000, Spectra/Por®). The retentate was aliquotted, frozen at −20° C., and used within one week.

All materials were studied in triplicate. Strips were cut into 11-mm×15-mm rectangular samples. Samples were individually placed in polystyrene cups and soaked overnight in cPBSzI at 4° C. (Sheu 1992:42). Prior to use, the buffer was degassed with a water-faucet aspirator (approximately 12–15 mm Hg) for at least 20 minutes, with stirring.

Following the overnight soak, the buffer was removed by aspiration and immediately replaced with 2.0 ml fresh, degassed cPBSzI. Protein was diluted in cPBSzI to a final concentration of 0.2 mg/ml. The mixture was spiked with $^{125}I$-fibrinogen to give a specific activity of 0.3 to 1×10$^6$ counts per minute per mg (cpm/mg).

Prior to the addition of the protein, samples were thermally equilibrated in a water bath at 37° C. for at least one hour. The protein solution also was equilibrated at 37° C. Adsorption was initiated by adding 0.5 ml fibrinogen (1 mg/ml). The protein solution was mixed by gentle repipetting to prevent foaming. Samples were incubated for two hours at 37° C.

Adsorption was terminated by dilution/displacement rinsing with 25 volumes cPBSzI (100 ml) per sample. The dilution/displacement method avoids exposing the adsorbate to air (e.g., Bergström et al. 1992). To apply a consistent rinse, an automated system was developed in which a syringe pump (Model 4200-17, Harvard Apparatus, South Natick, Mass.) delivered a 20-ml burst at 200 ml/minute, followed by a one second pause, then a final 80-ml burst at 200 ml/minute. This two-step procedure also permitted the segregation of liquid radioactive wastes of differing specific activities.

Samples were placed in 2.0 ml cPBSzI in polystyrene scintillation vials and gamma counted (Gamma Trac 1185, TM Analytic). From these results, the initial adsorption was calculated as the mass per fabric unit area (μg fibfinogen adsorbed/cm$^2$ of fabric). This calculation treats the samples as if they were smooth, planar surfaces, with a surface area of 2×1.1 cm×1.5 cm, or 3.3 cm$^2$.

After counting, samples were incubated in the cPBSzI for 24 hours ("soak-rinse;" Sheu 1992:42). The next day, they were dip rinsed, placed in clean counting tubes, and counted again to give a retained protein value. The results are summarized in Tables 1 and 2. The percent add-on shown in the tables was obtained with larger pieces of polymeric fabric which had been subjected to the wash procedure described above. As the tables indicate, Fabric A was coated with Surfactant A only, and Fabric B was coated with Surfactant B only.

TABLE 1

Summary of Radiolabeling Results with Fabric A Coated with Surfactant A

| Sample | Surfactant % Add-on[a] | Energy Density[b] | Nanograms Protein/cm$^2$ Fabric | |
|---|---|---|---|---|
| | | | Initial Value | Final Value |
| PF[c] | — | 0[d] | 352 ± 100 | 318 ± 97 |
| A1 | 0.58[e] | 0[d] | 240 ± 50 | 210 ± 41 |
| A2 | 0.58 | 12 | 180 ± 16 | 158 ± 16 |
| A3 | 0.58 | 22 | 88 ± 59 | 78 ± 56 |
| A4 | 0.58 | 60 | 35 ± 8 | 22 ± 2 |
| A5 | 0.58 | 120 | 59 ± 8 | 46 ± 10 |
| A6 | 0.58 | 219 | 114 ± 48 | 95 ± 41 |

[a]Percent by weight, based on the dry weight of the fabric.
[b]kJ m$^{-2}$.
[c]Original polymeric fabric (no surfactant coating).
[d]No corona treatment.
[e]Rounded off from 0.581 ± 0.059 from a set of replicate samples; a second set of three replicates gave a percent add-on of 0.066 ± 0.084 which was discounted as an anomaly.

TABLE 2

Summary of Radiolabeling Results with Fabric B Coated with Surfactant B

| Sample | Surfactant % Add-on[a] | Energy Density[b] | Nanograms Protein/cm$^2$ Fabric | |
|---|---|---|---|---|
| | | | Initial Value | Final Value |
| PF1[c] | — | 0[d] | 373 ± 10 | 354 ± 6 |
| PF2[c] | — | 110 | 742 ± 233 | 630 ± 230 |
| B1 | 0.7[e] | 0[d] | 216 ± 25 | 183 ± 24 |
| B2 | 0.7 | 12 | 104 ± 22 | 89 ± 18 |
| B3 | 0.7 | 22 | 77 ± 18 | 64 ± 16 |
| B4 | 0.7 | 110 | 29 ± 4 | 22 ± 4 |
| B5 | 0.7 | 120 | 32 ± 2 | 26 ± 2 |

[a]Percent by weight, based on the dry weight of the fabric.
[b]kJ m$^{-2}$.
[c]Original polymeric fabric (no surfactant coating).
[d]No corona treatment.
[e]Standard deviation was ±0.5, from a set of just two replicate samples.

Figure 2:
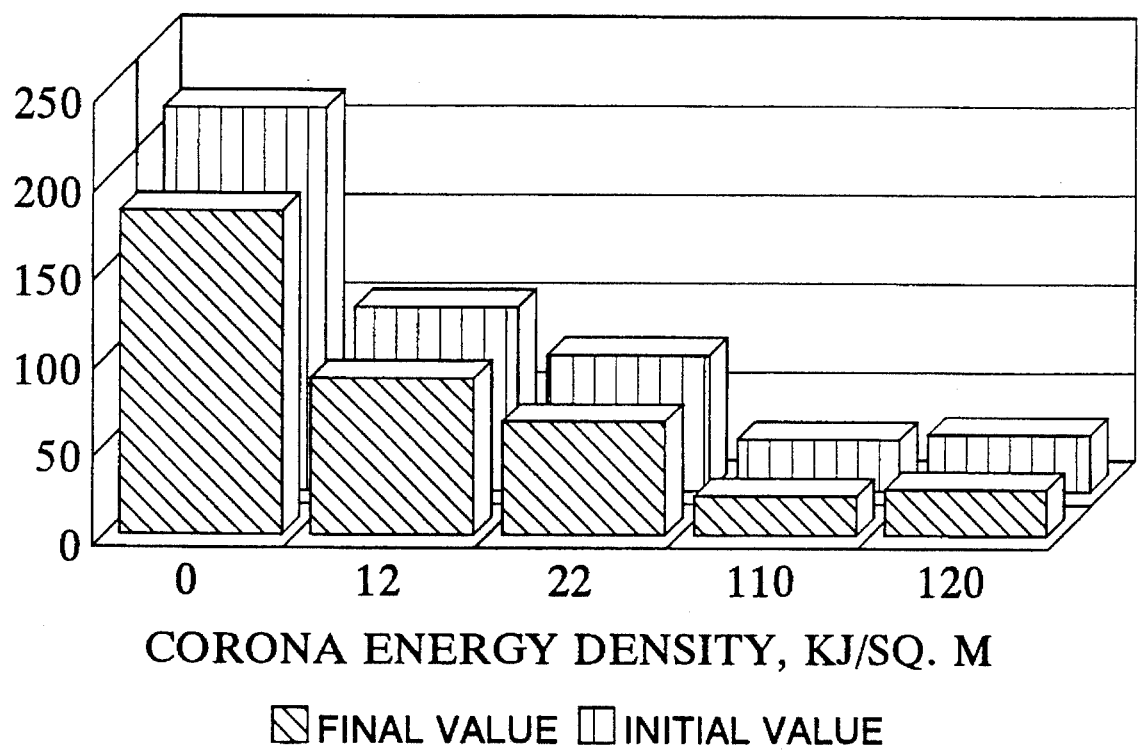

As an aid in understanding the data in the tables, the data for Samples A1–A6 were plotted as a three-dimensional bar graph which is shown in FIG. 1. Similarly, the data for Samples B1–B5 were plotted as a three-dimensional bar graph which is shown in FIG. 2. Each graph shows nanograms protein adsorbed per square centimeter of fabric as a function of corona energy density.

Upon comparing the data for Samples PF and A1 from Table 1 and Samples PF1 and B1 from Table 2, it is apparent that, in each case, the surfactant alone has only a modest effect on reducing protein adsorption by the polymeric fabric. While increasing the energy density initially resulted in decreases in the amount of protein adsorbed by the fabric, it is interesting to note that the highest energy density tested, i.e., an energy density of 219 kJ m$^{-2}$ resulted in increased protein adsorption. Thus, protein adsorption was at minimum levels in a range of energy densities of from about 35 to about 140 kJ m$^{-2}$.

It may be noted from the data for Samples PF1 and PF2 in Table 2 that corona discharge alone increases protein adsorption. When original polymeric fabric which had not been coated by a surfactant (Fabric B) was subjected to corona discharge at an energy density corresponding with minimum protein adsorption by Suffactant B-treated fabric, protein adsorption increased approximately two fold, compared to the same fabric which had not been corona treated.

The foregoing data are not sufficient to determine whether or not the corona treatments increased the durability of the two surfactants on the fabrics. Increases in surfactant durability, in theory, at least, could be responsible for the reduced protein adsorption which was observed. In order to resolve this issue, it was appropriate to examine add-on levels before and after washing fabrics that were treated with and without corona as summarized in Table 3. In the table, the columns headed "Before Wash" and "After Wash" refer to the rigorous washing protocol described above, to which each sample was subjected prior to exposure to protein.

TABLE 3

Summary of Add-On Levels Before and After Washing, With and Without Corona Treatments

| Surfactant | Fabric | Corona ED$^a$ | Percent Add-On Level | |
|---|---|---|---|---|
| | | | Before Wash | After Wash |
| A | A | 0 | 2.57 ± 0.18 | 0.32 ± 0.29 |
| | | 22 | 2.57 ± 0.18 | 0.37 ± 0.42 |
| | | 60 | 2.57 ± 0.18 | 0.02 ± 0.04 |
| | | 219 | 2.57 ± 0.18 | 0.24 ± 0.08 |
| B | B | 0 | 2.74 ± 0.0 | 0.71 ± 0.48 |
| | | 110 | 2.74 ± 0.0 | 0.60 |
| | | 120 | 2.74 ± 0.0 | 1.27 |

$^a$Corona energy density in kJ m$^{-2}$.

From the data in Table 3, it is evident that exposing a surfactant-treated sample of fabric to an air corona discharge has very little, if any, effect on the durability of the surfactant on the fabric. That is, the add-on levels obtained after washing corona-treated fabrics are essentially the same as the add-on levels obtained after washing fabrics without corona treatment.

Finally, samples of the fabrics used to generate the data in Tables 1 and 2 were used for ESCA analyses before and after washing, using the washing procedure as already described. Each sample of fabric was analyzed for siliconcarbon (Si/C) atomic ratios by electron spectroscopy for chemical analysis (ESCA), before and after washing. The ESCA data were obtained by Evans East, Plainsboro, New Jersey. The instrument employed was a Perkin-Elmer PHI Model 5000LS ESCA spectrometer utilizing a standard magnesium x-ray source. Source power was 400 watts. The analysis region was 1×3 mm and the exit angle was 45°. All samples were examined initially with low resolution survey scans to determine which elements were present and to establish initial atomic concentrations. High resolution ESCA multiplex data were taken to determine the atomic concentration and binding energy of the elements detected in the survey scans. A second survey spectrum was then collected to verify that sample damage had not occurred during acquisition of the multiplex data. The quantitation of the elements was accomplished by using the ESCA spectrometer as configured. Approximate sampling depth was 55 Å relative to carbon electrons. The Si/C atomic ratios from before washing and after washing were used to calculate a percent difference, as follows:

Percent Difference=100×[(Si/C before−Si/C after)÷Si/C before]

The results are summarized in Table 4.

TABLE 4

Summary of ESCA Si/C Atomic Ratios Before and After Washing, With and Without Corona Treatments

| Surfactant | Fabric | Corona ED$^a$ | ESCA Si/C Atomic Ratio | | Percent Difference$^b$ |
|---|---|---|---|---|---|
| | | | Before Wash | After Wash | |
| A | A | 0 | 0.166 | 0.072 | 57 |
| | | 12 | 0.183 | 0.094 | 49 |
| | | 22 | 0.185 | 0.108 | 42 |
| | | 60 | 0.215 | 0.191 | 11 |
| | | 120 | 0.240 | 0.217 | 10 |
| | | 219 | 0.264 | 0.288 | 0 |
| B | B | 0 | 0.165 | 0.086 | 48 |
| | | 12 | ND$^c$ | 0.172 | — |
| | | 22 | ND | 0.167 | — |
| | | 110 | 0.264 | 0.286 | 0 |
| | | 120 | 0.283 | 0.313 | 0 |

$^a$Corona energy density in kJ m$^{-2}$.
$^b$The difference between the "Before Wash" and "After Wash" values, expressed as a percent.
$^c$Not determined The data in Table 4 make clear two consequences of corona treatments on Si/C atomic ratios. First, corona treatment reduces the difference between the "Before Wash" and "After Wash" values. In other words, as the corona energy density increases, the Si/C atomic ratio after washing approaches the Si/C atomic ratio before washing. Second, corona treatment causes the Si/C atomic ratio before washing to exceed the atomic ratio before washing without any corona treatment. Moreover, these consequences occur even though it is apparent that corona treatment does not increase the durability of surfactant on the fabric.

Figure 3:
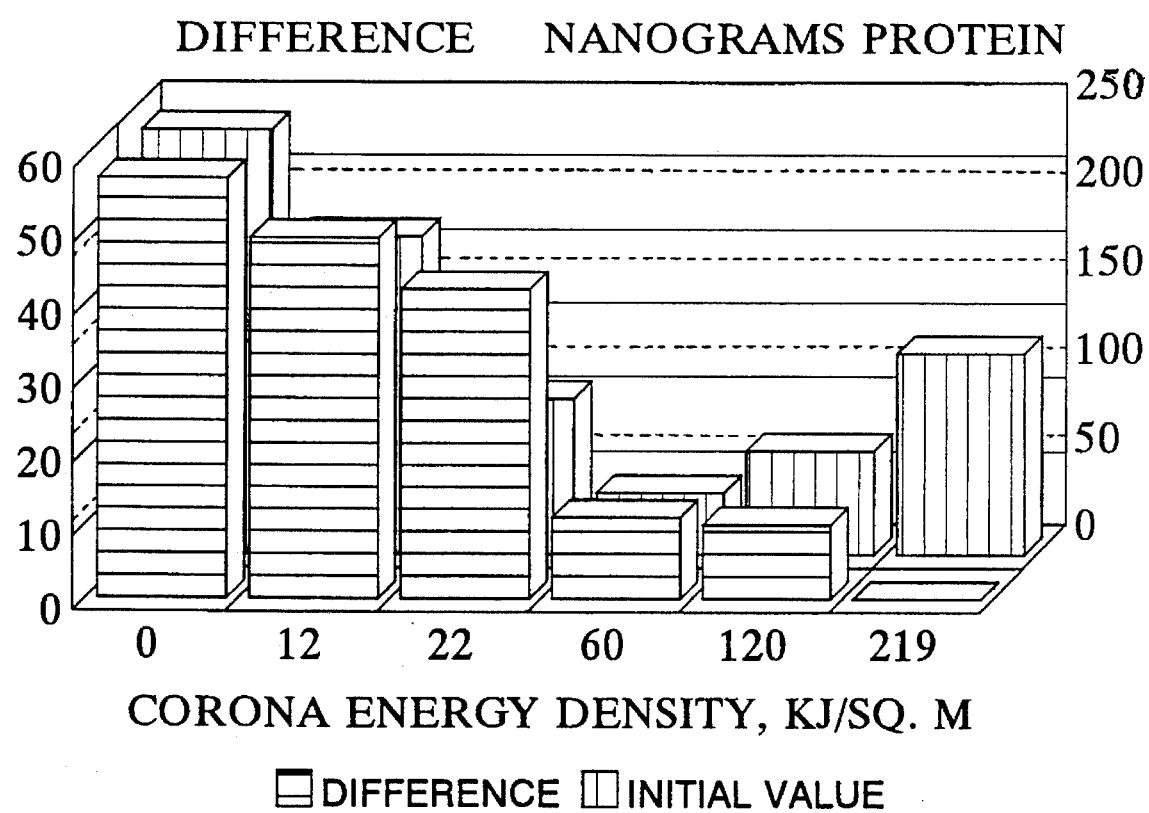
FIG. 3 is a three-dimensional bar graph showing the differences in ESCA silicon/carbon atomic ratios before and after washing, as a function of corona energy density. Included in the figure is the initial value bar graph from FIG. 1.

The data in Table 4 for the Surfactant A/Fabric A combination were plotted as a three-dimensional bar graph, with corona energy density on the x-axis and the difference calculation being on the y-axis, left-hand side. The data from Table 1 for the same combination also were included in the plot, shown in FIG. 3, with nanograms protein per square centimeter of fabric being on the y-axis, right-hand side. Except for the difference values at energy densities of 22 and 219 kJ m$^{-2}$, the plots are remarkably similar.

Having thus described the invention, numerous changes and modifications thereof will be readily apparent to those having ordinary skill in the art without departing from the spirit or scope of the invention.

What is claimed is:

1. A coated polymeric fabric which comprises:

a base ply of a polymeric fabric having a surface; and a surfactant on the surface of the fabric; in which the surfactant is adapted to reduce the adsorption of protein by the polymeric fabric, is present on the fabric in an amount of at least about 0.3 percent by weight, based on the weight of the fabric, and has the general formula,

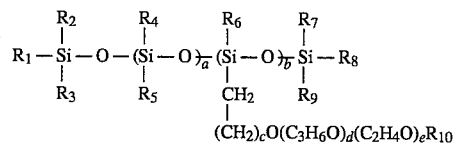

wherein:

each of $R_1$–$R_9$ independently is selected from the group consisting of $C_1$–$C_8$ alkyl and aryl groups;

$R_{10}$ is hydrogen or a $C_1$–$C_4$ alkyl group;

a represents an integer from about 20 to about 100;

b represents an integer from about 4 to about 10;

c represents an integer from 1 to about 10;

d represents an integer from about 0 to about 30;

e represents an integer from about 0 to about 30;

the sum of d and e is in a range of from about 5 to about 60; and the number-average molecular weight of the surfactant is in a range of from about 5,000 to about 60,000;

and the coated polymeric fabric has been treated by air corona discharge at a corona energy density of from about 10 to about 280 kilojoules per square meter.

2. The coated polymeric fabric of claim 1, in which the polymeric fabric is a polyolefin fabric.

3. The coated polymeric fabric of claim 1, in which the surfactant has a solubility in water at 20° C. no greater than about 10 percent by weight, based on the weight of the water.

4. The coated polymeric fabric of claim 1, in which:

each of $R_1$–$R_9$ independently is selected from the group consisting of $C_1$–$C_4$ alkyl and phenyl groups;

$R_{10}$ is hydrogen or a $C_1$–$C_4$ alkyl group;

a represents an integer from about 30 to about 90;

b represents an integer from about 4 to about 10;

c represents an integer from 2 to about 4;

d represents an integer from about 5 to about 25;

e represents an integer from about 5 to about 25;

the sum of d and e is in a range of from about 10 to about 50;

the ratio of e to d is in a range of from about 10 to about 0.1; and the number-average molecular weight of the surfactant is in a range of from about 5,000 to about 40,000.

5. A disposable absorbent article, at least one component of which is the coated polymeric fabric of claim 1.

6. A coated polyolefin fabric which comprises:

a base ply of a polyolefin fabric having a surface; and a surfactant on the surface of the fabric; in which the surfactant is present on the fabric in an amount of at least about 0.3 percent by weight, based on the weight of the fabric, and has the general formula,

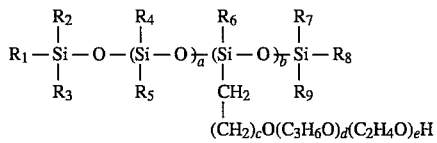

wherein:

each of $R_1$–$R_9$ independently is selected from the group consisting of $C_1$–$C_8$ alkyl and aryl groups;

$R_{10}$ is hydrogen or a $C_1$–$C_4$ alkyl group;

a represents an integer from about 20 to about 100;

b represents an integer from about 4 to about 10;

c represents an integer from 1 to about 10;

d represents an integer from about 0 to about 30;

e represents an integer from about 0 to about 30;

the sum of d and e is in a range of from about 5 to about 60; and the number-average molecular weight of the surfactant is in a range of from about 5,000 to about 60,000; and the coated polymeric fabric has been treated by air corona discharge at a corona energy density of from about 10 to about 280 kilojoules per square meter.

7. The coated polymeric fabric of claim 6, in which:

each of $R_1$–$R_9$ independently is selected from the group consisting of $C_1$–$C_4$ alkyl and phenyl groups;

$R_{10}$ is hydrogen or a $C_1$–$C_4$ alkyl group;

a represents an integer from about 30 to about 90;

b represents an integer from about 4 to about 10;

c represents an integer from about 2 to about 4;

d represents an integer from about 5 to about 25;

e represents an integer from about 5 to about 25;

the sum of d and e is in a range of from about 10 to about 50;

the ratio of e to d is in a range of from about 10 to about 0.1; and the number-average molecular weight of the surfactant is in a range of from about 5,000 to about 40,000.

8. A disposable absorbent article, at least one component of which is the coated polymeric fabric of claim 6.

9. The disposable absorbent article of claim 8, in which said disposable absorbent article is a diaper.

10. The disposable absorbent article of claim 8, in which said disposable absorbent article is a feminine care product.

11. The disposable absorbent article of claim 10, in which said disposable absorbent article is a sanitary napkin.

12. The disposable absorbent article of claim 10, in which said disposable absorbent article is a tampon.

13. The disposable absorbent article of claim 8, in which said disposable absorbent article is an incontinent product.

14. The disposable absorbent article of claim 8, in which said disposable absorbent article is a training pant.

15. The disposable absorbent article of claim 8, in which said disposable absorbent article is a wipe.

16. A method of reducing the adsorption of protein by a polymeric fabric which comprises:

providing a polymeric fabric having a surface;

applying to the surface of the polymeric fabric a composition comprising water and a surfactant adapted to reduce the adsorption of protein by the polymeric fabric; and treating the fabric to which a surfactant has been applied by air corona discharge at a corona energy density of from about 10 about 280 kJ m$^{-2}$;

in which the surfactant has the general formula,

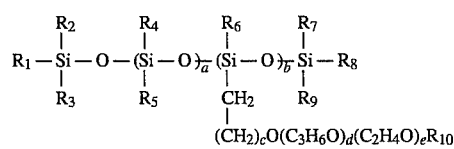

wherein:

each of $R_1$–$R_9$ independently is selected from the group consisting of $C_1$–$C_8$ alkyl and aryl groups;

$R_{10}$ is hydrogen or a $C_1$–$C_4$ alkyl group;

a represents an integer from about 20 to about 100;

b represents an integer from 4 to about 10;

c represents an integer from 1 to about 10;

d represents an integer from about 0 to about 30;

e represents an integer from about 0 to about 30;

the sum of d and e is in a range of from about 5 to about 60; and the number-average molecular weight of the surfactant is in a range of from about 5,000 to about 60,000.

17. The method of claim 16, in which the polymeric fabric is a polyolefin fabric.

18. The method of claim 16, in which the polymeric fabric is dried prior to treating the fabric by air corona discharge.

19. The method of claim 16, in which the surfactant has a solubility in water at 20° C. no greater than about 10 percent by weight, based on the weight of the water.

20. The method of claim 16, in which:

each of $R_1$–$R_9$ independently is selected from the group consisting of $C_1$–$C_4$ alkyl and phenyl groups;

$R_{10}$ is hydrogen or a $C_1$–$C_4$ alkyl group;

a represents an integer from about 30 to about 90;

b represents an integer from about 4 to about 10;

c represents an integer from 2 to about 4;

d represents an integer from about 5 to about 25;

e represents an integer from about 5 to about 25;

the sum of d and e is in a range of from about 10 to about 50;

the ratio of e to d is in a range of from about 10 to about 0.1; and the number-average molecular weight of the surfactant is in a range of from about 5,000 to about 40,000.

* * * * *